United States Patent
Jacobsen et al.

(10) Patent No.: US 6,802,821 B2
(45) Date of Patent: Oct. 12, 2004

(54) DIALYZER

(75) Inventors: Veronica Lee Jacobsen, Sandy, UT (US); Stephen Kuykendall, North Ogden, UT (US); Olli Touminen, North Ogden, UT (US); Troy McGhee, North Ogden, UT (US)

(73) Assignee: Fresenius USA, Inc., Lexington, MA (US)

( * ) Notice: Subject to any disclaimer, the term of this patent is extended or adjusted under 35 U.S.C. 154(b) by 104 days.

(21) Appl. No.: 09/969,123

(22) Filed: Oct. 1, 2001

(65) Prior Publication Data

US 2003/0065283 A1 Apr. 3, 2003

(51) Int. Cl.[7] .......................... A61M 37/00; C02F 1/44
(52) U.S. Cl. .................. 604/6.09; 604/5.04; 210/646; 210/321.72; 210/321.79; 210/321.81; 210/321.88
(58) Field of Search ...................... 604/6.09, 5.04, 604/6.05, 6.06; 422/44–48; 210/645, 646, 321.71, 321.72, 321.79, 321.8, 321.88, 321.89, 456, 500.23

(56) References Cited

U.S. PATENT DOCUMENTS

| | | | |
|---|---|---|---|
| 4,116,841 A | * | 9/1978 | Borsanyi ............... 210/321.77 |
| 4,201,673 A | | 5/1980 | Kanno et al. |
| 4,219,426 A | | 8/1980 | Spekle et al. |
| 4,288,494 A | * | 9/1981 | Porter et al. ................ 428/398 |
| 4,334,993 A | * | 6/1982 | Norton .................... 210/321.8 |
| 5,160,615 A | * | 11/1992 | Takagi et al. ............ 210/321.8 |
| 5,297,591 A | * | 3/1994 | Baurmeister ........... 139/383 R |
| 5,817,278 A | * | 10/1998 | Fini et al. ..................... 422/45 |
| 6,074,559 A | | 6/2000 | Hahmann et al. |

FOREIGN PATENT DOCUMENTS

| | | |
|---|---|---|
| FR | 2542203 | 9/1984 |
| JP | 1996-08-280796 | 10/1996 |

* cited by examiner

Primary Examiner—Angela D. Sykes
Assistant Examiner—Leslie R. Deak
(74) Attorney, Agent, or Firm—Gibson, Dunn & Crutcher LLP

(57) ABSTRACT

A dialyzer design that includes a potting material encasing a microfiber bundle in each end of a cylindrical body. The potting material is set by spinning the dialyzer in a centrifuge to force the potting material to the ends of the dialyzer interior chamber, where it sets with a non-planar surface. Dialysate fluid distribution rings define a space between the dialyzer interior chamber and dialyzer inlet and outlet ports, and laterally support the microfiber bundle against the dialysate fluid flow pressure. The dialysate fluid distribution ring circumferential edge substantially conforms to the non-planar potting material surface, to ensure that the lateral support to the microfiber bundle is constant, thereby lessening distortion, rupturing and obstruction of the microfibers.

5 Claims, 2 Drawing Sheets

DIALYZER

FIELD OF THE INVENTION

This invention relates to the field of dialyzers typically used in hemodialysis and related medical procedures, and in particular to a design having a lengthened useful life, together with a method for manufacturing the same.

BACKGROUND OF THE INVENTION

Patients with kidney disease suffer from the adverse effects of toxin build-up in their blood. Dialysis is a process which employs an artificial kidney to remove those toxins. In hemodialysis a dialyzer is used which contains a semi-permeable membrane dividing the dialyzer into two chambers. Blood is pumped through one chamber and a dialysis solution through the second. As the blood flows by the dialysis fluid, separated by the semi-permeable membrane, blood impurities such as urea and creatinine diffuse through the semi-permeable membrane into the dialysis solution by the diffusion, convection and absorption. The electrolyte concentration of the dialysis fluid is set so as to maintain electrolytic balance within the patient.

Dialyzers often use a large number of microfibers encased in a chamber. The chamber is often a hollow cylinder open at both ends. Thousands of hollow semipermeable microfibers carry blood from one end to the opposite end so that blood flows through the microfibers in a first direction. Dialysate ports are also present on opposite ends of the chamber. One port carries dialysate into the chamber, the dialysate flows through the chamber in a countercurrent direction to the blood flow, and the other port carries the dialysate out of the chamber. The solute removal thus takes place across the semipermeable membrane that is the microfiber wall. This design produces a high surface area for solute removal in a relatively low volume device.

One significant challenge is to connect the microfiber interior channels to the blood lines, so that blood flows smoothly from the arterial blood line, into the microfiber interior channels where it can pass into and through the dialyzer chamber, and out the other end of the microfiber interior channels to the venous blood line.

This is done by filling the open-ended cylinder-shaped dialyzer chamber with microfibers extending in the longitudinal direction. Each end of the cylinder is threaded to receive a cap closing the end. The dialyzer is then positioned in a centrifuge to allow rotation about an axis perpendicular to the central longitudinal axis, wherein the axis of rotation extending through the midpoint of the cylinder. A liquid potting material such as epoxy or urethane is then injected into the dialysate ports on each end of the chamber, and the dialyzer is spun in the centrifuge. The centripetal force produced by the rotation in the centrifuge forces the potting material to each end, where it sets and hardens.

The dialysate ports in the cylinder wall near each end of the dialyzer present special challenges. It is desirable for the microfibers to be supported by the cylinder wall throughout their length, or as much of their length as possible, so that the dialysate fluid flow pressure on the microfibers does not distort them. Such distortion can result in their breaking, which allows mingling of blood and dialysate, or can obstruct the flow of blood through the microfiber interior channels.

Support for the microfibers is achieved in some designs by separating the dialysate ports from the dialyzer chambers with a dialysate fluid distribution ring. The dialysate fluid distribution ring is effectively an extension of the dialyzer cylinder wall. The dialysate port accesses the dialyzer chamber by means of an intermediate space defined at the radial inner side by the dialysate fluid distribution ring and at the radially outer side by an outer wall. The dialysate fluid distribution ring thus extends lateral support to the microfibers around the circumference of the microfiber bundle while still enhancing dialysate fluid distribution between the dialysate ports and the chamber.

In practice, this design is quite effective. It has been discovered, however, that the microfibers tend to fail first at a particular location due apparently to an artifact of the potting process. As the dialyzer is spun in a centrifuge to force potting material to each end to encase the microfibers, the surface closest to the axis of spinning rotation assumes a curve. It is believed that this is because the centripetal force exerted on the potting material is in proportion to the distance of the potting material from the axis of rotation, much as the outward force on a merry-go-round is greater at the edge than at the center. In order to maintain constant centripetal force along the potting material surface during the centrifuge operation, that surface assumes a curvature that maintains a constant distance from the axis of centrifuge rotation. That resulting curvature departs slightly from the plane resulting from cutting off the ends of the potting material to expose the microfiber interior channels.

Like the cut-off end of the potting material, the dialysate fluid distribution ring edge has in the past been planar. Because the dialysate fluid distribution ring edge has been planar while the potting material surface has been curved, the width of the gap between the dialysate fluid distribution ring edge and the potting material has varied. This gap represents the space in which the microfiber bundle is unsupported by the dialyzer cylinder wall or by the dialysate fluid distribution ring. The dialysate fluid flow pressure between the microfiber interior channel and the dialyzer chamber interior tends to flex or distort the microfibers. Because pressure produces a force in proportion to the area on which it acts, the force produced at areas of relatively large gap between the dialysate fluid distribution ring edge and the potting material surface is different from the force produced at areas of relatively small gap between the dialysate fluid distribution ring edge and the potting material surface. It has been found that this differential force is responsible for much of the microfiber distortion, rupturing and obstruction seen in the initial stages of dialyzer destruction.

It is desirable for dialyzers to be filled with microfibers in a manner that supports the dialysate fluid flow pressure on the microfiber bundle in a uniform way to avoid differential forces on the microfibers which distorts, ruptures or obstructs them.

SUMMARY OF THE INVENTION

The present invention overcomes the deficiencies of existing systems by use of a novel design for the dialyzer dialysate fluid distribution ring. This dialysate fluid distribution ring separates the dialyzer interior chamber from the dialysate ports. The dialysate fluid distribution ring edge distal from the centrifuge axis of rotation assumes a shape defined as an annulus cut by a cylinder perpendicular to the axis of the annulus.

DETAILED DESCRIPTION OF A PREFERRED EMBODIMENT

Figure 1:
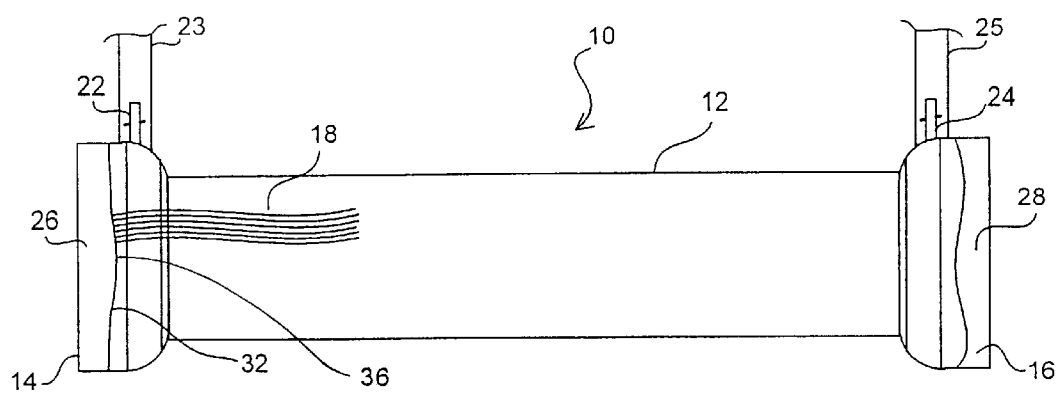
FIG. 1 shows a dialyzer in accordance with a preferred embodiment of the invention.

A dialyzer 10 in accordance with a preferred embodiment of the invention is shown in FIG. 1. The overall shape of the dialyzer 10 is cylindrical, comprising a cylindrical body 12, a blood line inlet end 14 and a blood line outlet end 16.

The ends 14 and 16 are preferably enlarged compared to the chamber body to accommodate a distribution ring described below. Proximate to the blood inlet end 14 is a dialysate outlet port 22, and proximate to the blood outlet end 16 is a dialysate inlet port 24. The cylindrical body 12 is filled with a microfiber bundle 18, only a fragment of which is shown in FIG. 1 for purposes of clarity. The microfibers 18 are potted in a polyurethane potting material 26 and 28 at each end 14 and 16. The dialysate inlet port 24 connects to a dialysate inlet line 25, and the dialysate outlet port 22 connects to a dialysate outlet line 23.

Figure 2:
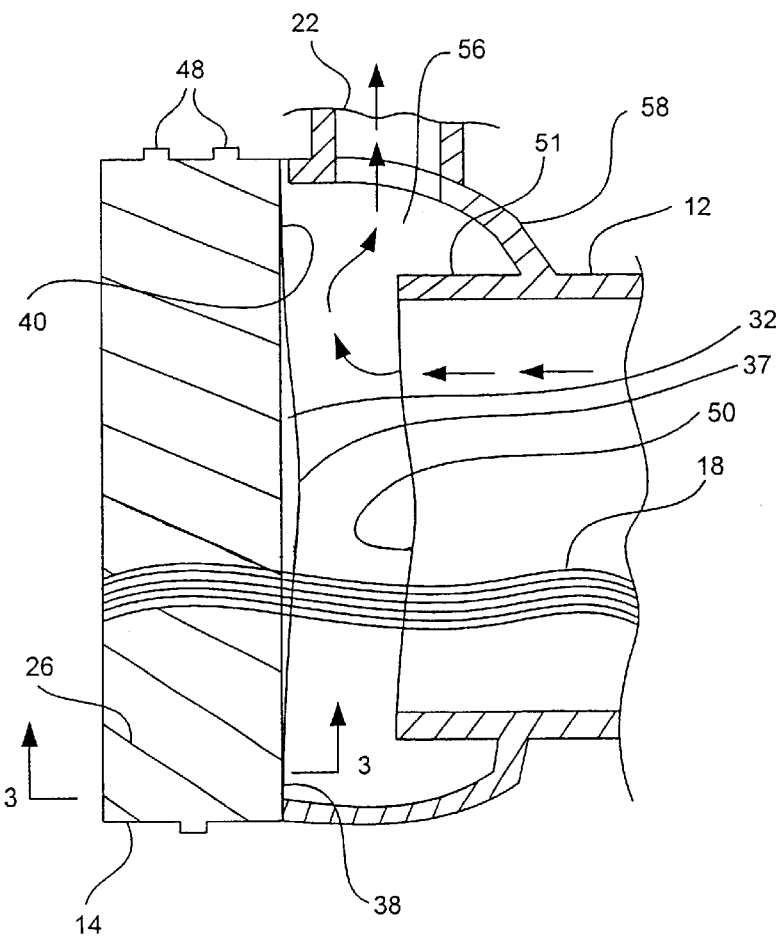
FIG. 2 shows an enlarged cross-section view through the center of one end of the dialyzer of FIG. 1.
Figure 3:
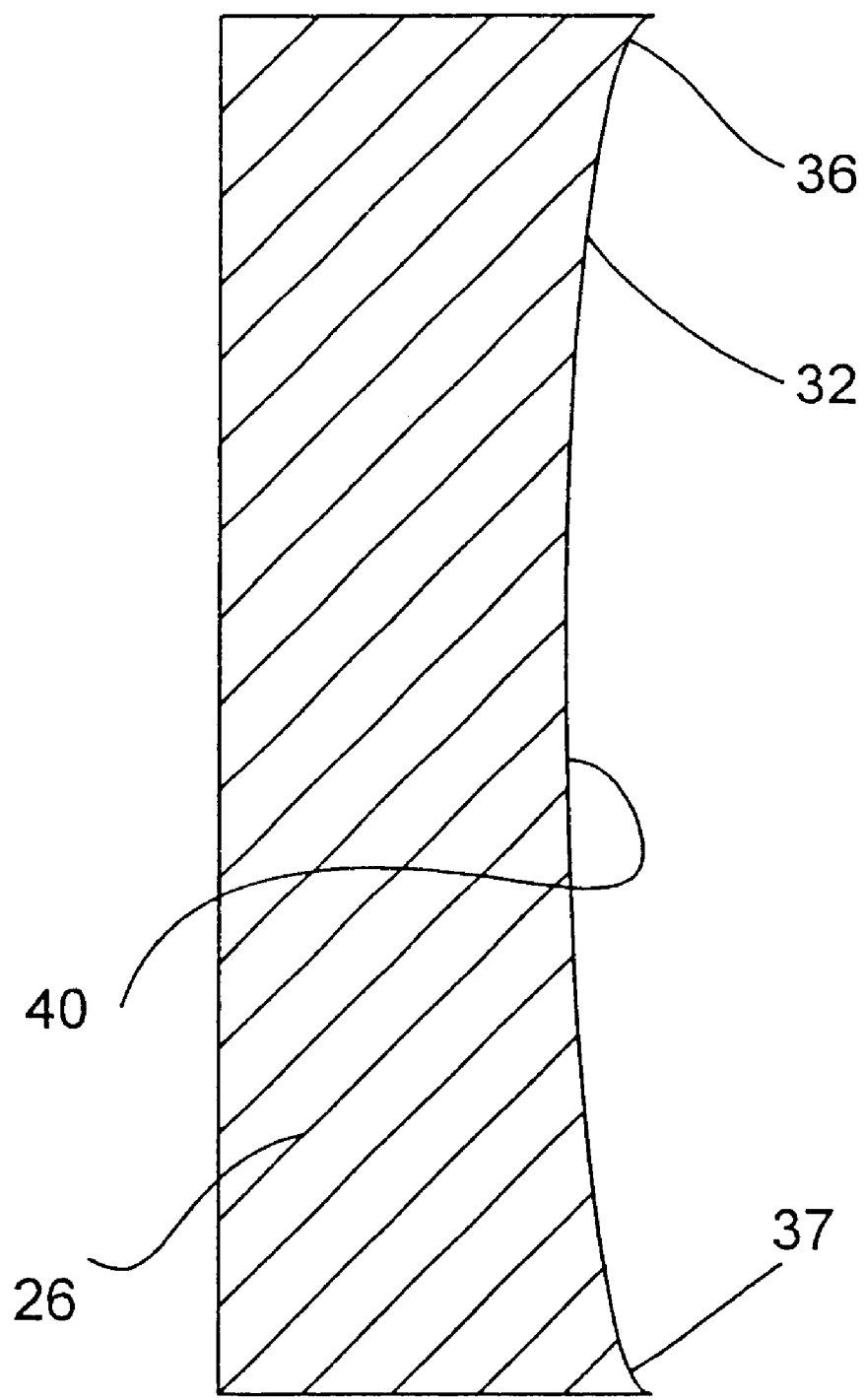
FIG. 3 shows an enlarged cross-section view through the center of the end of the dialyzer of FIG. 2 viewed in the direction indicated by line 3–3, omitting all but the potting material for clarity.

An enlarged sectional view of one end 14 of the dialyzer 10 is shown in FIG. 2 and FIG. 3. FIG. 3 omits all but the potting material for clarity. A portion of the microfiber bundle 18 is shown in FIG. 2, embedded in the potting material 26, while the rest of the microfiber bundle 18 is omitted for clarity. As the figures show, the interior surface 32 of the potting material 26 is not planar. Rather, geometrically speaking, it is the surface defined by the intersection of a cylinder with another cylinder. In this case, the first cylinder is the potting material 26. The intersecting, or cutting, cylinder which defines the potting material surface is an imaginary cylinder with a longitudinal axis extending up and down and intersecting with the longitudinal coaxial axes of the potting material 26 cylinder and the dialyzer cylindrical body 12. The resultant interior surface 32 of the potting material 26 has a circumferential edge that undulates. The overall thickness of the potting material 26 thus varies from relatively thick at two opposite points 36 and a point 37 opposite 36, to relatively thin at two opposite points that are offset 90° from point 36, at points 38 and 40.

The potting material 26 ensures that the blood is confined to the interior channels of the microfiber bundle, and is unable to leak into the dialyzer chamber. A fitting (not shown) threaded onto the threads 48 of the dialyzer ends 14 and 16 serve to connect the blood lines to the dialyzer ends 14 and 16. Blood thereby flows from the arterial blood line into the interior bundle of the microfibers of the microfiber bundle 18, through the microfiber interior channels from one end 14 to the other end 16 of the dialyzer, and into the venous blood line (not shown) via another fitting (not shown) connecting that end 16 to the venous blood line.

A set of threads 48 is molded into the dialyzer 10 ends 14 and 16 to allow the ends to be capped during the step of centrifuging the potting material into the dialyzer chamber, and also to allow attachment to a fitting for connection to the blood lines. This portion of the manufacturing process is known in the art, and is not further described here.

The design and configuration of the dialysate fluid distribution ring 51 is evident from FIG. 2. The dialysate fluid distribution ring 51 is an annular extension of the cylindrical dialyzer body 12. The dialyzer end 14 is radially spaced away from the dialysate fluid distribution ring 51 to define an annular space 56 between the end housing 58 and the dialysate fluid distribution ring 51.

In operation, blood flows from an arterial blood line (not shown) and into the interior channels of the microfibers comprising the microfiber bundle 18. At the same time, dialysate flows in the countercurrent direction to the blood flow. Dialysate flows from the inlet dialysate line 24 and through the inlet port 24 to enter the interior chamber of the dialyzer 10. The dialysate flows through the dialyzer interior chamber on the outside of the microfibers. The blood is thus separated from the dialysate by the semi-permeable membranes of the microfiber walls, which allow the transfer of liquids, toxins and nutrients by the diffusion, convection, and absorption. The dialysate then exits the dialyzer 10 through the dialysate outlet port 22 and into the dialysate outlet line 23.

The dialysate fluid distribution ring circumferential edge 50 in past designs has been planar. Because the potting material 26 surface is not planar, due to the effect of the centrifugal molding process, the result in past designs has been a varying gap between the potting material surface and the dialysate fluid distribution ring circumferential edge. Because the dialysate fluid distribution ring 51 provides support to the microfiber bundle 18 against the dialysate fluid flow pressure exerted during dialysis procedures, this support varies along the circumference of the dialysate fluid distribution ring 51 edge in past designs. This varying support tends to distort, rupture or obstruct the microfibers.

As show in FIG. 2, the design of the dialysate fluid distribution ring 51 circumferential edge 50 in the present invention is not planar. It instead is of an undulating shape that conforms to the undulating shape of the potting material 26 surface. This results in a gap between the potting material 26 surface and the dialysate fluid distribution ring 51 circumferential edge 50 that does not vary but is instead substantially constant.

This substantially constant gap allows for substantially constant support of the microfiber bundle 18. "Substantially constant gap" means for purposes of the claims below a gap which may be, but is not necessarily, exactly uniform, but which varies by an amount that lessens the distortion, rupturing or obstruction of the microfibers in comparison to the prior art planar circumferential edge of the dialysate fluid distribution ring.

Results of experimental tests show that the non-planar distribution ring of the present invention does indeed lessen the failure rate of the dialyzer. Three types of dialyzers were tested: prototypes having the novel distribution ring design described herein; production samples of Model F80A of Fresenius Medical Care; and Model CA210 of Baxter Laboratories.

The pressure used in this testing was 50 psi and the flow rate was 4 gpm per dialyzer. The testing included several phases for each cycle: phase 1 included 3 seconds of flow through the dialysate port only; phase 2 included 3 seconds of flow through the blood port only, phase 3 included 3 seconds of flow through the dialysate and blood ports, and phase 4 was 3 seconds with no flow. Each "cycle was defined as 11 minutes of sequential and repetitious 4-phase testing.

The results are presented in the table below, which shows the number of dialysis cycles completed before each failure for each sample, the average number of such cycles for each of the three designs, and the Standard Deviation. At the end of each cycle of testing, the dialyzers were tested for a bubble point failure to detect the fiber shear. If the dialyzer failed the bubble point test, then it was categorized as failed due to a fiber shear.

| Sample Type: F80A | Failed Cycle | Sample Type: Prototype | Failed Cycle | Sample Type: Baxter CA 210 | Failed Cycle |
|---|---|---|---|---|---|
| Sample 1 | 1 | Sample 1 | 26 | Sample 1 | 1 |
| Sample 2 | 4 | Sample 2 | 14 | Sample 2 | 1 |
| Sample 3 | 1 | Sample 3 | 14 | Sample 3 | 1 |
| Sample 4 | 1 | Sample 4 | 12 | Sample 4 | 1 |
| Sample 5 | 1 | Sample 5 | 7 | Sample 5 | 1 |
| Sample 6 | 1 | Sample 6 | 25 | Sample 6 | 1 |
| Sample 7 | 1 | Sample 7 | 7 | Sample 7 | 1 |
| Sample 8 | 1 | Sample 8 | 26 | Sample 8 | 1 |
| Sample 9 | 6 | Sample 9 | 12 | Sample 9 | 1 |
| Sample 10 | 1 | Sample 10 | 8 | Sample 10 | 1 |
| Average S.D. | 1.8 cycles 1.75 | Average S.D. | 15.1 cycles 7.74 | Average S.D. | 1 cycle 0 |

It can be seen from these results that the design with a novel distribution ring in accordance with the present invention showed a much lower failure rate, or much higher number of cycles before failure. While these tests do not purport to duplicate exactly any actual dialysis procedure, it is believed that they fairly predict relative failure rates in such procedures.

What is claimed is:

1. A dialyzer, comprising: a cylindrical body having a first end and a second end, the body having an interior with a set of semi-permeable microfibers extending from the first and to the second end; a dialysate inlet port proximate the first end and a dialysate outlet port proximate the second end; wherein the microfibers are encased in a first potting material at the first end and a second potting material of the second end, wherein the potting materials surround and encase the microfibers in the body, and the potting materials each have an interior surface with an undulating circumferential edge; a first annular shaped dialysate fluid distribution ring proximate the first end and a second annular shaped dialysate fluid distribution ring proximate the second end, the dialysate fluid distribution rings dividing the body interior from the ports, wherein the dialysate fluid distribution rings each have an undulating circumferential edge that are a substantially constant distance from the undulating circumferential edges of the potting material.

2. The dialyzer of claim 1, wherein the undulating circumferential edges of the potting materials and the dialysate fluid distribution rings are geometrically defined by a first cylinder intersecting a second cylinder, wherein said first cylinder is represented by the potting materials and the dialysate fluid distribution rings having coaxial axes, and said second cylinder is an imaginary intersecting or cutting cylinder with a longitudinal axis that intersects perpendicularly said coaxial axes.

3. The dialyzer of claim 1, wherein the undulating circumferential edge of the potting materials defines a variable thickness of the potting material that includes a first pair of relatively thick opposite edges extending toward the body middle in relation to a second pair of relatively thin opposite edges at approximately 90° from the first pair of relatively thick opposite edges.

4. The dialyzer of claim 1, wherein said distance is between one-eighth and three-eights inch.

5. The dialyzer of claim 1, wherein said distance is between one-fifth and one-fourth inch.

* * * * *